(12) United States Patent
Pelletier et al.

(10) Patent No.: US 8,388,745 B1
(45) Date of Patent: Mar. 5, 2013

(54) REPLACEABLE SIEVE BED FOR PORTABLE OXYGEN CONCENTRATOR

(75) Inventors: Dana G. Pelletier, Ortonville, MI (US); Michael S. McClain, Ortonville, MI (US); Michael P. Chekal, Brighton, MI (US)

(73) Assignee: Oxus America, Inc., Rochester Hills, MI (US)

( * ) Notice: Subject to any disclaimer, the term of this patent is extended or adjusted under 35 U.S.C. 154(b) by 177 days.

(21) Appl. No.: 12/942,514

(22) Filed: Nov. 9, 2010

Related U.S. Application Data

(60) Provisional application No. 61/259,239, filed on Nov. 9, 2009.

(51) Int. Cl.
*B01D 53/02* (2006.01)

(52) U.S. Cl. ............... 96/108; 96/134; 96/147; 96/151; 96/152

(58) Field of Classification Search .............. 95/90–148; 96/108–134; 128/204.18–205.27; 55/DIG. 33
See application file for complete search history.

(56) References Cited

U.S. PATENT DOCUMENTS

| | | | | |
|---|---|---|---|---|
| 4,687,573 | A * | 8/1987 | Miller et al. | 210/143 |
| 5,672,195 | A * | 9/1997 | Moreau et al. | 95/96 |
| 6,019,823 | A * | 2/2000 | Tischler et al. | 96/108 |
| 6,585,810 | B1 * | 7/2003 | Gaita et al. | 96/135 |
| 2007/0227360 | A1 * | 10/2007 | Atlas et al. | 96/121 |
| 2008/0028933 | A1 * | 2/2008 | Ross et al. | 95/138 |
| 2009/0065007 | A1 * | 3/2009 | Wilkinson et al. | 128/205.27 |

* cited by examiner

*Primary Examiner* — Duane Smith
*Assistant Examiner* — Phillip Shao
(74) *Attorney, Agent, or Firm* — Young Basile

(57) ABSTRACT

A sieve module includes an impermeable housing and an adsorptive media bed. The impermeable housing is puncturable at a first puncture location to receive gas from an exterior of the impermeable housing. The impermeable housing is also puncturable at a second puncture location to expel gas to the exterior of the impermeable housing. The adsorptive media bed is disposed within the impermeable housing. The gas flows through the impermeable housing from the first puncture wound to the second puncture location by flowing through the adsorptive media bed.

10 Claims, 4 Drawing Sheets

REPLACEABLE SIEVE BED FOR PORTABLE OXYGEN CONCENTRATOR

CROSS-REFERENCE TO RELATED APPLICATIONS

This application claims the benefit of U.S. Provisional Patent Application Ser. No. 61/259,239, which was filed on Nov. 9, 2009.

FIELD OF THE INVENTION

The invention relates to the field of portable oxygen concentrators, and more particularly, to a portable oxygen concentrator having replaceable sieve beds.

BACKGROUND OF THE INVENTION

Portable oxygen concentrators are well-known. Portable oxygen concentrators process ambient air to separate the nitrogen that is present in the ambient air from the oxygen that is present in the ambient air. A common application for portable oxygen concentrators is in the field of medical use. In medial applications, the oxygen is then delivered to a patient, typically through a nasal cannula.

Portable oxygen concentrators for medical use typically operate using a pressure swing adsorption (PSA) cycle. In the pressure swing adsorption cycle, the portable oxygen concentrator compresses air to between 7 and 40 psig and passes the compressed air through columns known as sieve beds. The sieve beds are filled with a zeolite material that adsorbs nitrogen from the compressed ambient air. The remaining oxygen is passed to the end of the column in a concentration that is typically greater than 90%, whereas ambient oxygen concentration is 20.9%.

After the concentrated oxygen is utilized, the portable oxygen concentrator depressurizes the sieve bed. Depressurization of the sieve bed allows the adsorbed nitrogen to exit the zeolite, and the nitrogen is then purged from the sieve bed.

As a result of the cycle of pressurization, adsorption, depressurization, and purging that occurs within the sieve bed, a single sieve bed cannot provide a continuous stream of oxygen. For this reason, portable oxygen concentrators for medical use typically contain two or more sieve beds. While one or more of the sieve beds are being pressurized, the remaining sieve beds are purged. This provides a constant supply of oxygen to the patient. In addition, in typical portable oxygen concentrators, each sieve bed relies upon one or more of the other sieve beds for proper operation. In particular, purging of a sieve bed is accomplished utilizing some of the product gas from one of the other sieve beds. Thus, a fault in one sieve bed diminishes the performance of the remaining sieve beds.

Ideally, portable oxygen concentrators for medical use are small, lightweight, operate quietly, are capable of at least two hours of continuous battery operation, have a life expectancy of at least two years without failure, and are able to withstand normal indoor and outdoor temperature and humidity conditions. These features provide patients with mobility and independence, and do so with a low cost of ownership.

Ultimately, it is desirable to have an oxygen concentrator that is dependable and requires minimal maintenance. One potential maintenance concern associated with portable oxygen concentrators is degradation of the zeolite material. In particular, the zeolite material will degrade over time if it comes in contact with the liquid water that condenses out of the ambient air during parts of the PSA cycle. It is this liquid water, as opposed to vapor phase water, that causes degradation of the zeolite. Thus, if the PSA cycle is run continuously without employing preservation techniques, the zeolite will degrade such that the oxygen concentration produced by the sieve bed falls below acceptable levels. Depending on the humidity in the ambient air, this level of zeolite degradation could take anywhere from a few days to over a month.

Because portable oxygen concentrators are intended to have at least a two year life expectancy and operate in warm and humid environments, conventional portable oxygen concentrators are designed to prevent degradation of zeolite material. Such designs often significantly increase the complexity of the portable oxygen concentrator. Strategies typically employed include using significantly more zeolite than would be required for dry air, using higher pressures than would be required for dry air, inclusion of sensing electronics to monitor ambient temperature and humidity conditions, as well as structures intended to prevent a liquid water from reaching the zeolite, such as condensers, dryers, and venturi tubes, or use of a vacuum during the purge cycle in an attempt to remove liquid water from the zeolite. As a result of provision of these types of features, portable oxygen concentrators tend to suffer from disadvantages including one or more of added costs, increased size, increased weight, noisiness, or shortened battery operation time.

The zeolite material is inexpensive in comparison to the hardware and software solutions that are been utilized in an effort to prevent the zeolite material from degrading. However, the zeolite material in conventional portable oxygen concentrators is not easily replaceable.

It would be desirable to provide a portable oxygen concentrator having replaceable, disposable sieve beds, thereby obviating the need for hardware and software solutions that are intended to preserve the zeolite material.

SUMMARY OF THE INVENTION

The invention provides a replaceable, disposable sieve bed for portable oxygen concentrators that may be easily replaced by the end user of the portable oxygen concentrator.

The sieve module includes an impermeable housing and an adsorptive media bed. The impermeable housing is puncturable at a first puncture location to receive gas from an exterior of the impermeable housing and is puncturable at a second puncture location to expel gas to the exterior of the impermeable housing. The adsorptive media bed is disposed within the impermeable housing. The gas flows through the impermeable housing from the first puncture location to the second puncture location by flowing through the adsorptive media bed.

The impermeable housing may have a first end and a second end. The first puncture location and the second puncture location may both be located at the first end of the impermeable housing.

The sieve module may also include a divider structure that defines a first area and a second area within the impermeable housing. The first puncture location is located at the first area, and the second puncture location is located at the second area. The divider is configured such that the first area and the second area are in fluid communication solely at the second end of the impermeable housing.

Alternatively, the sieve module may include a divider structure that is configured to direct the gas from the first puncture location to the second end of the impermeable housing prior to contact of the gas with the adsorptive media bed. The divider structure is further configured to direct the gas through the adsorptive media bed as it travels from the second end of the impermeable housing to the second puncture location.

The divider may define a passageway that conducts the gas from the first puncture location to the second end of the impermeable housing prior to contact of the gas with the adsorptive media bed. In particular, the divider may include a tube that extends from the first end of the impermeable housing toward the second end of the impermeable housing, wherein the passageway is defined by the interior of the tube.

The sieve module may also include a diffuser that is in communication with the passageway and the adsorptive media bed for supplying the gas to the adsorptive media bed. The diffuser may include a perforated separator that is connected to the tube and extends transverse to the tube. In such a configuration, the adsorptive media bed may be disposed between the first end of the impermeable housing and the perforated separator. Furthermore, a gas permeable filler material may be disposed between the second end of the impermeable housing and the perforated separator.

A crushable material may be disposed adjacent to the first end of the impermeable housing directly adjacent to the second puncture location. Furthermore, the crushable material may be interposed between the first end of the impermeable housing and the adsorptive media bed to space the adsorptive media bed from the first end of the impermeable housing.

The impermeable housing may include a first end wall, a second end wall, and a peripheral wall. The first end wall is located at the first end of the impermeable housing, while the second end wall is disposed at the second end of the impermeable housing. The peripheral wall extends from the first end wall to the second end wall. In this configuration, the impermeable housing may include a first portion and a second portion. The first portion defines the first end wall of the impermeable housing. The second portion defines both the second end wall and the peripheral wall of the impermeable housing. The first and second portions of the impermeable housing are each unitary structures. The first portion of the impermeable housing is connected to the second portion of the impermeable housing to define an interior for the impermeable housing that is sealed with respect to ambient air prior to puncturing of the impermeable housing at the first puncture location or the second puncture location. Furthermore, the impermeable housing may be fabricated from aluminum.

Finally, the adsorptive media bed of the sieve module may include a zeolite material as the primary component thereof.

BRIEF DESCRIPTION OF THE DRAWINGS

The description herein makes reference to the accompanying drawings, wherein like-referenced numerals refer to like parts throughout the several views, and wherein.

DETAILED DESCRIPTION

Figure 1:
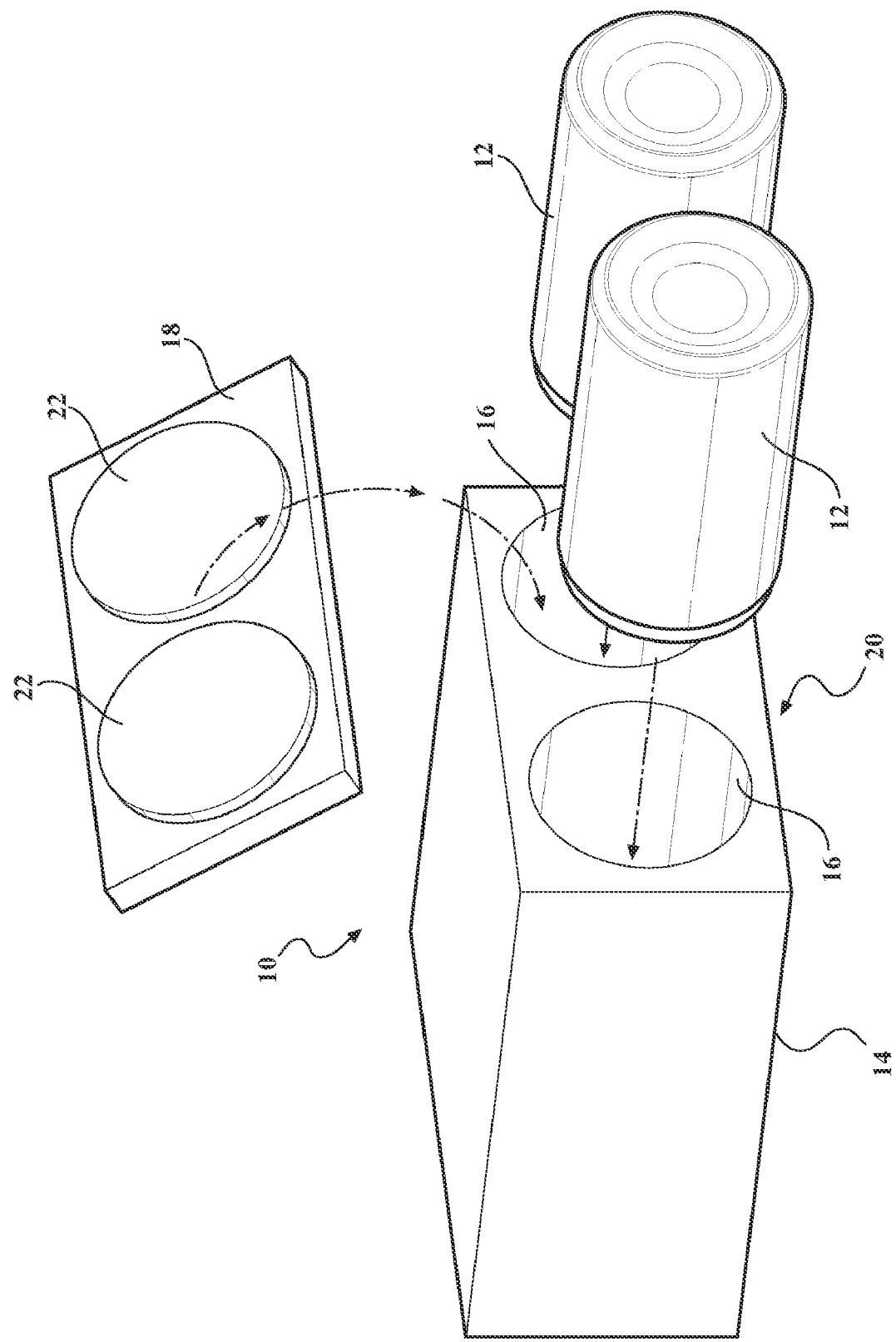
FIG. 1 is a perspective view showing a portable oxygen concentrator according to the invention including two disposable sieve beds according to the invention.
Figure 2:
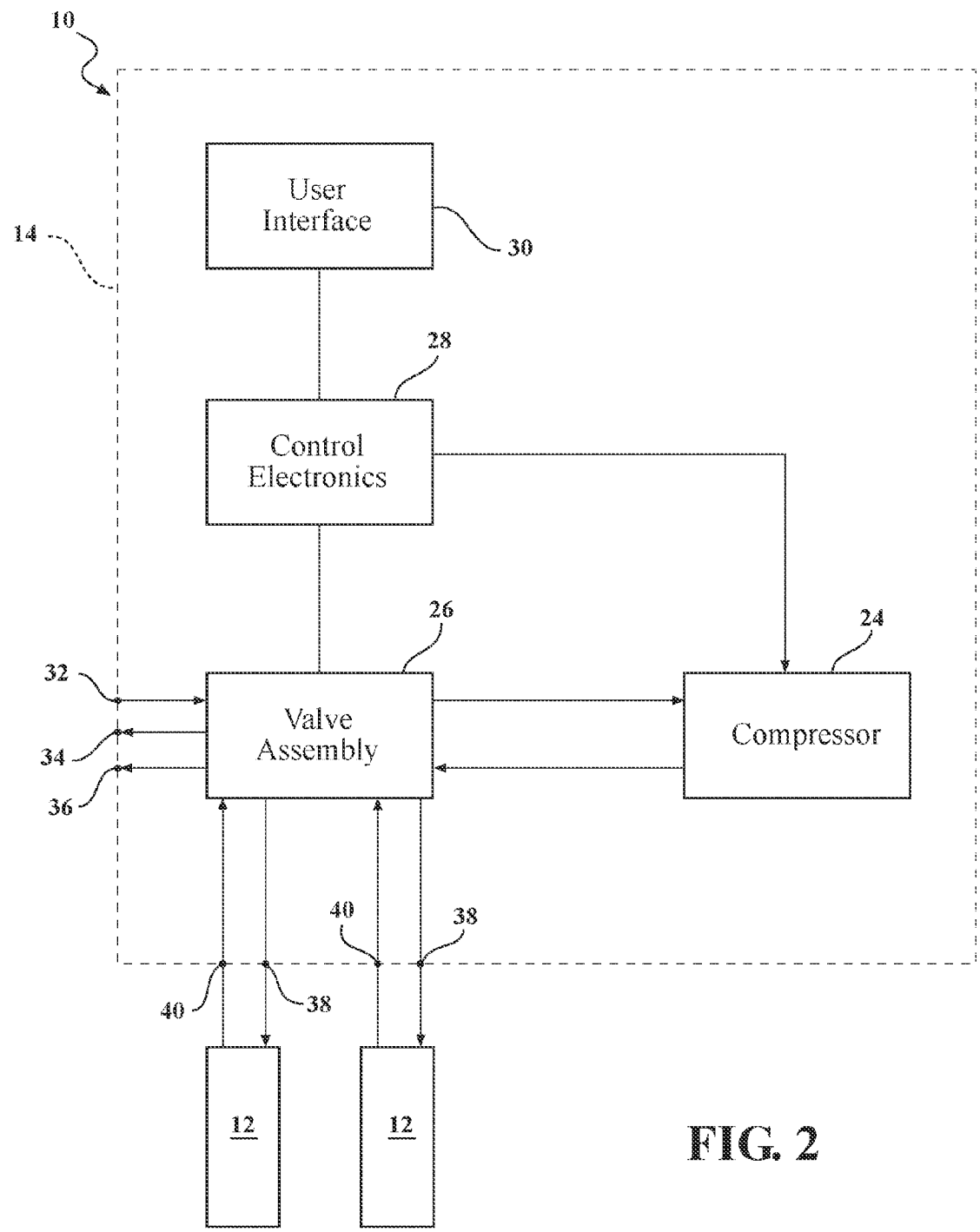
FIG. 2 is a block diagram showing the main components of the portable oxygen concentrator according to the invention.

FIGS. 1-2 show an oxygen concentrator 10 and sieve modules 12 according to the present invention. As will be further explained herein, the oxygen concentrator 10 is intended to be a portable unit. However, the invention described herein is not limited to portable oxygen concentrators, but rather, could be embodied in a non-portable unit as well. The oxygen concentrator 10 preferably utilizes two or more of the sieve modules 12 in order to allow continuous operation of the oxygen concentrator 10. As will be explained further herein, the sieve modules 12 are replaceable, disposable, and are designed to be installed and removed with respect to the oxygen concentrator 10 by the end user of the oxygen concentrator 10.

The oxygen concentrator 10 includes a housing 14 in which the components of the oxygen concentrator 10 and the sieve modules 12 are contained. One or more cavities 16 are defined by the housing 14 for receiving the sieve modules therein. In particular, a single cavity 16 could be provided for each individual sieve module 12. Accordingly, the cavities 16 could correspond in number to the sieve modules 12. Alternatively, multiple sieve modules 12 could be provided within a single cavity 16.

The housing 14 of the oxygen concentrator 10 may include a door 18 or other suitable structure at an open end 20 of the cavities 16. The door 18 closes the cavities 16 with respect to the exterior of the housing 14 and retains the sieve modules 12 within the housing. The door 18 is connected to the remainder of the housing 14 by a hinge or other suitable structure that allows opening and closing of the door 18 with respect to the cavity 16 of the housing 14. A compliance pad 22 may be provided on the door 18 for engagement with the sieve modules to take up tolerance variations and assist in retaining the sieve modules 12 within the cavities 16.

The oxygen concentrator 10 operates on a pressure swing adsorption (PSA) cycle. Accordingly, components are provided within the housing 14 of the oxygen concentrator 10 for facilitating such a cycle, as is well known in the art. These components may include a compressor 24, a valve assembly 26, control electronics 28, a user interface 30, an ambient air intake 32, a waste gas outlet 34, and a cannula port 36.

The valve assembly 26 of the oxygen concentrator 10 is also connected to a sieve module inlet port 38, as well as a sieve module outlet port 40. The sieve module inlet port 38 is utilized to supply gas to the sieve module 12 from the exterior of the sieve module 12. The sieve module outlet port 40 is utilized to receive gas that is expelled from the sieve module 12 to the exterior of the sieve module 12.

Figure 3:
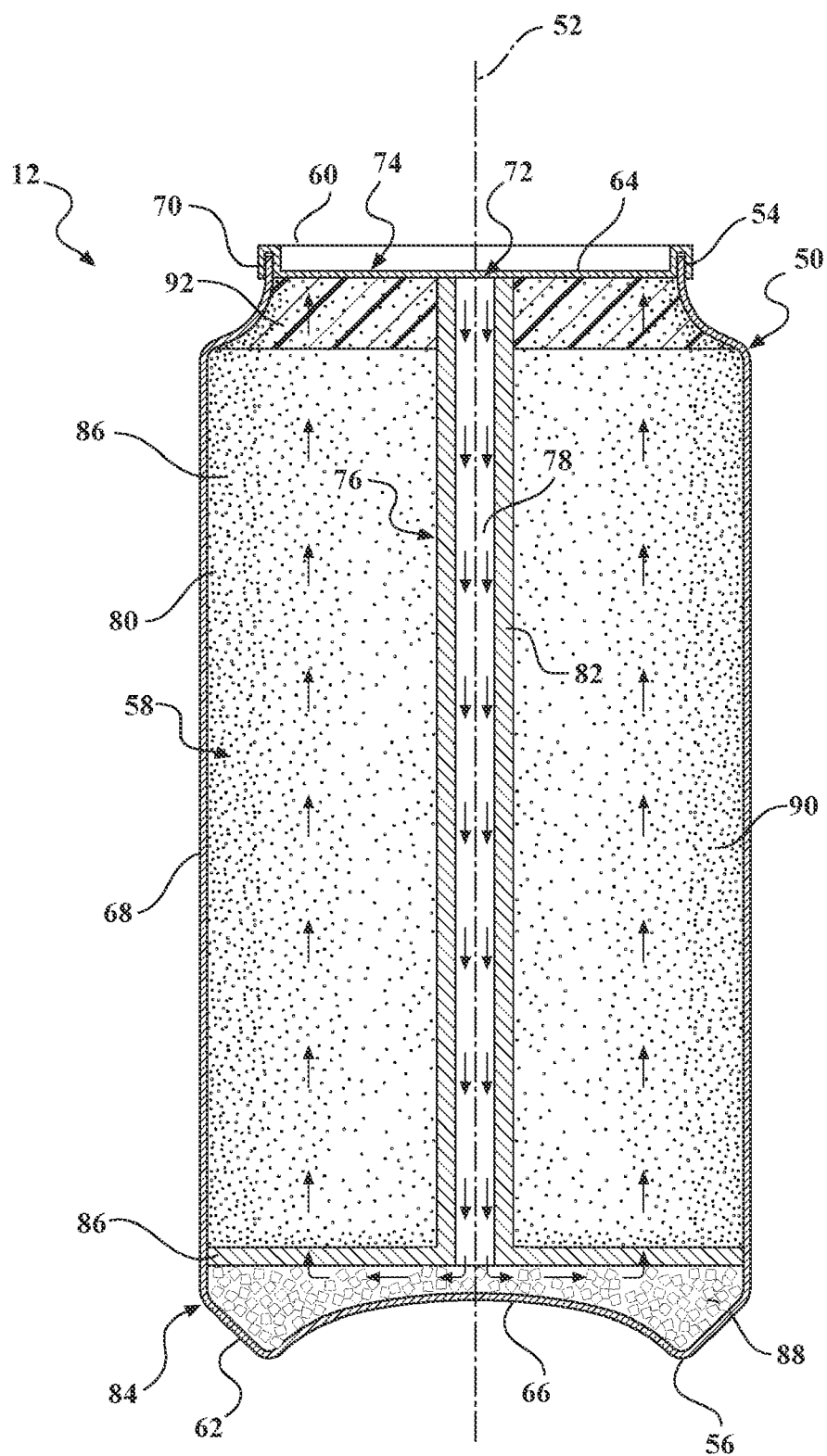
FIG. 3 is a cross-sectional view of the disposable sieve bed according to the invention.

As shown in FIG. 3, the sieve module 12 includes an impermeable housing 50 in which all of the components of the sieve module 12 are contained. The housing 50 of the sieve module 12 extends along a longitudinal axis 52 between a first end 54 and a second end 56. As shown and described herein, the housing 50 of the sieve module 12 has a generally cylindrical shape, similar to a conventional aluminum soda can. However, it should be understood that the sieve module 12 is not limited to this geometry, and any other suitable geometry could be provided.

The housing 50 defines an interior 58 for the sieve module 12. The interior 58 is sealed prior to use of the sieve module 12 with the portable oxygen concentrator 10. This may be accomplished by fabricating the housing 50 of the sieve module 12 from two or more portions that are connected together in a sealed manner such that the interior 58 of the housing 50 is sealed with respect to ambient air exterior to the housing 50.

In order to define the interior 58, the housing 50 may include a first portion 60 and a second portion 62. The first and second portions 60, 62 of the housing 50 are each impermeable unitary structures that are fabricated from aluminum or another suitable material.

The first portion 60 defines a first end wall 64 for the housing 50. The first end wall 64 is located at the first end 54 of the housing 50, is generally planar, and extends generally transverse to the longitudinal axis 52 of the housing 50.

The second portion 62 of the housing 50 defines a second end wall 66 and a peripheral wall 68 for the housing 50. The second end wall 66 is located at the second end 56 of the housing 50 and extends generally transverse to the longitudinal axis 52 of the housing 50. The peripheral wall 68 of the second portion 62 is formed integrally with the second end wall 66 and extends from the second end wall 66 at the second end 56 of the housing 50 to the first end wall 64 at the first end 54 of the housing 50.

The first and second portions 60, 62 of the housing 50 are connected to one another at a joint 70 where the peripheral wall 68 of the second portion 62 meets the first end wall 64 of the first portion 60. The joint 70 serves to seal the interior 58 of the housing 50 and may be any suitable manner of structure, such as a crimp, adhesive, soldered joint, welded joint, or similar structures.

As will be explained further herein, fluid communication between the interior 58 of the sieve module 12 and the sieve module inlet and outlet ports 38, 40 of the oxygen concentrator 10 is accomplished by puncturing the first end wall 64 of the housing 50 of the sieve module 12. More particularly, the first end wall 64 of the housing 50 of the sieve module 12 is puncturable at a first puncture location 72 to receive gas from an exterior of the housing 50 and is puncturable at a second puncture location 74 to expel gas to the exterior of the housing 50.

Introducing and expelling gas with respect to the sieve module 12 at a single end of the housing 50 is in contrast to typical sieve bed design, wherein the sieve bed is linear, such that gas is introduced at a first end of the sieve bed and expelled at a second end of the sieve bed. Thus, to accommodate both introduction and expulsion of gas at a single end of the housing 50 of the sieve module 12, structures are provided to create a flow path through the interior of the housing 50 along which gas may travel from the first puncture location 72 to the second puncture location 74.

The first and second puncture locations 72, 74 may be placed anywhere on the first end wall 64, subject to the requirement that the internal structure of the sieve module 12 must be configured in accordance with the first and second puncture locations 72, 74. However, the first and second puncture locations 72, 74 are preferably radially symmetrical, such that a cylindrical housing 50 could be installed with respect to the oxygen concentrator 10 without regard to its radial alignment, which would obviate the need for keying or other similar strategies for ensuring proper radial alignment of the sieve module 12 with respect to the oxygen concentrator 10.

In order to establish a desired flow path within the housing 50 of the sieve module 12, the sieve module 12 includes a divider structure 76. The divider structure 76 serves to divide the interior 58 of the housing 50 into a first area 78 and a second area 80 at the first end 54 of the housing 50 adjacent to the first end wall 64. The first puncture location 72 is located at the first area 78 of the interior 58 of the housing 50. The second puncture location 74 is located at the second area 80 of the interior 58 of the housing 50. As will be explained more fully herein, the divider structure 76 is configured such that the first area 78 and the second area 80 are in fluid communication solely at the second end 56 of the housing 50.

The divider structure 76 includes a tube 82 that extends from the first end wall 64 of the housing 50 toward the second end wall 66 of the housing 50. In particular, the tube 82 extends a majority of the distance from the first end wall 64 to the second end wall 66 and terminates near, but spaced from, the second end wall 66. The tube 82 has a hollow interior that defines the first area 78. Consequently, the second area 80 is defined within the housing 50 external to the tube 82.

A diffuser 84 is positioned within the housing 50 at the second end 56 of the housing 50. The diffuser 84 serves to evenly distribute the gas into an adsorptive media bed 90 that is located within the housing 50 in the second area 80 thereof. Diffusion at the diffuser 84 occurs after the gas travels to the second end 56 of the housing 50 from the first puncture location 72 by way of the tube 82 of the divider structure 76.

The diffuser 84 includes a gas permeable separator 86 that is connected to the tube 82, extends substantially transverse to the tube 82, and itself may be considered part of the divider structure 76. The diffuser 84 also includes a gas permeable filler material 88 that is disposed within the housing 50 at the second end 56 thereof between the gas permeable separator 86 and the second end wall 66 of the housing 50. The gas permeable filler material is in fluid communication with the interior of the tube 82 such that it receives gas from the tube 82 and allows the gas to expand within the gas permeable filler material 88 at the second end 56 of the housing 50. The gas permeable filler material 88 may be any material that is suitable for allowing the gas to expand within this space. In order to reduce the amount of moisture reaching the adsorptive media bed, however, the gas permeable filler material 88 could be a desiccant material, such as silica gel. It will be understood that the diffuser 84 also functions to retain the adsorptive media bed 90 within the second area 80 of the housing 50. This ensures that the gas travels from the first puncture location 72 to the second end 56 of the housing 50 prior to contact between the gas and the adsorptive media bed 90.

Within the second area 80 of the housing 50, adjacent to the first end wall 64, a crushable material 92 is provided within the housing 50. The crushable material 92 may be present directly adjacent to all portions of the first end wall 64 of the housing 50 within the second area 80 of the interior 58 of the housing 50, such that the adsorptive media bed 90 is spaced from the first end wall 64 of the housing 50. The crushable material 92 may be a crushable foam. The crushable material 92 is disposed directly adjacent to the second puncture location 74, such that puncturing occurs within the crushable material 92 and not within the adsorptive media bed 90. This helps prevent or reduce leakage of the zeolite material of the adsorptive media bed 90 from the housing 50 after it is removed from the oxygen concentrator 10.

The adsorptive media bed 90 is disposed within the second area 80 of the interior 58 of the housing 50. The adsorptive media bed 90 extends continuously within this space and is bounded by the crushable material 92 near the first end 54 of the housing 50, is bounded by the diffuser 84 near the second end 56 of the housing 50, and is also bounded by the peripheral wall 68 of the housing 50. The tube 82 of the divider structure 76 extends through or adjacent to the adsorptive media bed 90. The adsorptive media bed 90 preferably includes a zeolite material for separating nitrogen from the ambient air. However, it should be understood that other adsorptive materials that are able to separate nitrogen from oxygen could be utilized.

Figure 4:
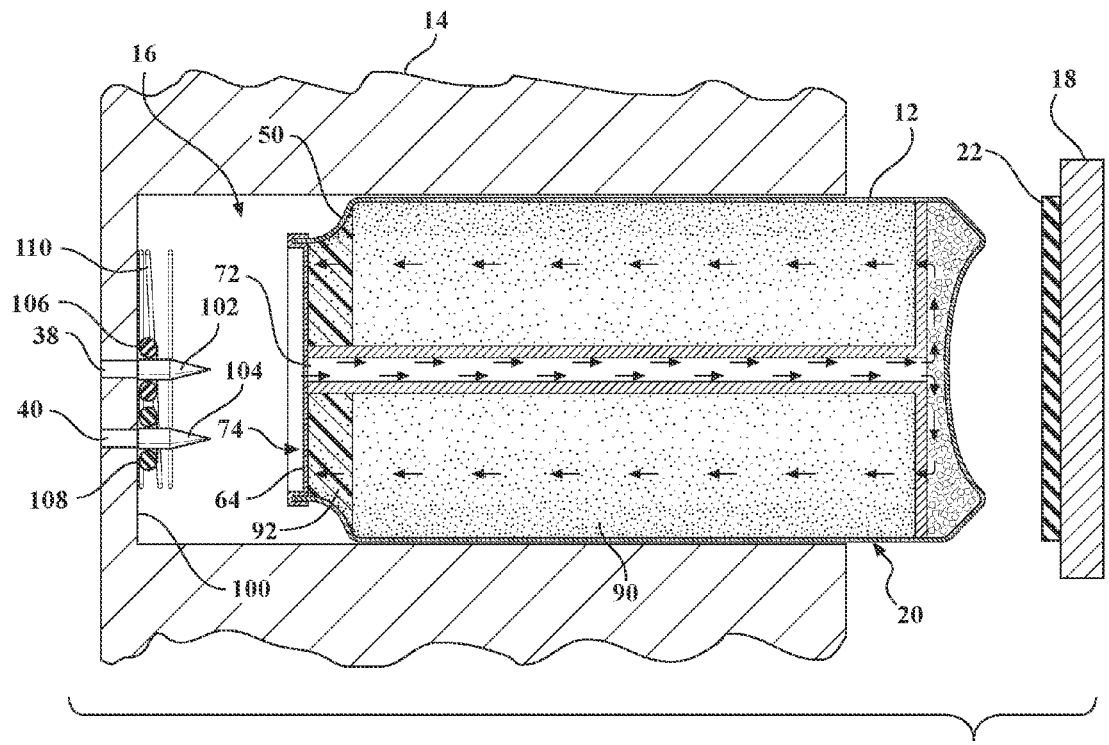
FIG. 4 is a cross-sectional view of the portable oxygen concentrator according to the invention showing a sieve bed in a partially inserted position.

FIG. 4 shows the sieve module 12 partially inserted with respect to the cavity 16 of the oxygen concentrator 10. At an internal end wall 100 of the cavity 16, opposite the open end 20, a first puncturing member 102 and a second puncturing member 104 are positioned within the cavity 16 such that they extend toward the open end 20 of the cavity 16, from the internal end wall 100 of the cavity 16, to which the first and second puncturing members 102, 104 are connected. The first and second puncturing members 102, 104 are in fluid communication with the sieve module inlet port 38 and the sieve module outlet port 40, respectively.

The first and second puncturing members 102, 104 are any suitable structure capable of piercing the first end wall 64 of the housing 50. Thus, the first and second puncturing members 102, 104 may be barbs, needles, or similar structures. O-rings 106, 108 are positioned on each of the second puncturing members for preventing leaks between the first and second puncturing members 102, 104 and the interior 58 of the housing 50 subsequent to installation of the sieve module 12 with respect to the oxygen concentrator 10 by puncturing the first end wall 64 using the first and second puncturing members 102, 104. Adjacent to the first and second puncturing members 102, 104, a biasing member 110, such as a spring, is positioned on the internal end wall 100 of the cavity 16. The biasing member 110 engages the sieve module 12 and biases the sieve module 12 away from the internal end wall 100 of the cavity 16. This facilitates removal of spent sieve modules 12 from the cavity 16.

Figure 5:
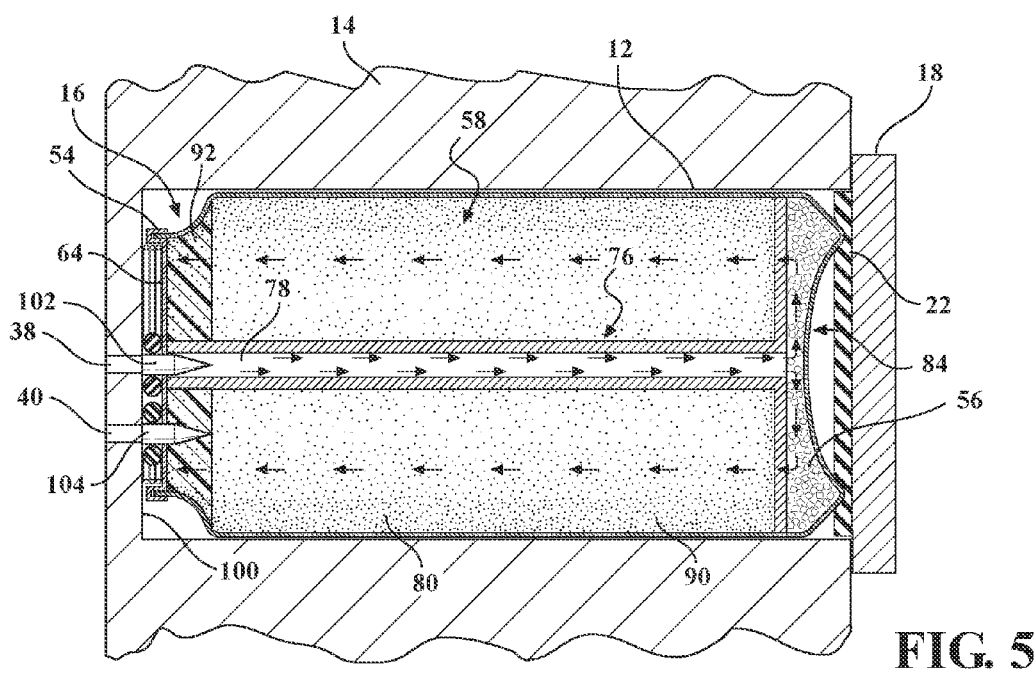
FIG. 5 is a cross-sectional view of the portable oxygen concentrator according to the invention showing a sieve bed in an installed position with respect to the portable oxygen concentrator.

As shown in FIG. 5, installation of the sieve module 12 with respect to the cavity 16 is completed by inserting the sieve module 12 into the cavity 16 until the first and second puncturing members 102, 104 have punctured the first end wall 64 of the housing 50. Once this is done, the first puncturing member 102 is disposed within the first area 78 of the interior 58 of the housing 50. The second puncturing member 104 is disposed within the second area 80 of the interior 58 of the housing 50. Thus, upon supply of gas from the sieve module inlet port 38, the gas travels through the first puncturing member 102 and is supplied to the interior 58 of the sieve module 12. Then, as a result of the configuration of the divider structure 76, the gas that is supplied from the sieve module inlet port 38 travels to the second end 56 of the housing 50 before entering the adsorptive media bed 90 by way of the diffuser 84. The gas then travels through the adsorptive media bed 90, where adsorption is performed by the zeolite material within the adsorptive media bed 90. Then, the gas may exit the sieve module 12 through the second puncturing member 104 into the sieve module outlet port 40.

While the invention has been described in connection with certain embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A sieve module, comprising:
    an impermeable housing that is puncturable at a first puncture location to receive gas from an exterior of the impermeable housing and is puncturable at a second puncture location to expel gas to the exterior of the impermeable housing;
    an adsorptive media bed that is disposed within the impermeable housing, wherein the gas flows through the impermeable housing from the first puncture location to the second puncture location by flowing through the adsorptive media bed;
    the impermeable housing having a first end and a second end, wherein the first puncture location and the second puncture location are both located at the first end of the impermeable housing; and
    a divider that defines a first area and a second area within the housing, the first puncture location being located at the first area and the second puncture location being located at the second area, and the divider configured such that the first area and the second area are in fluid communication solely at the second end of the impermeable housing.

2. A sieve module, comprising:
    an impermeable housing that is puncturable at a first puncture location to receive gas from an exterior of the impermeable housing and is puncturable at a second puncture location to expel gas to the exterior of the impermeable housing;
    an adsorptive media bed that is disposed within the impermeable housing, wherein the gas flows through the impermeable housing from the first puncture location to the second puncture location by flowing through the adsorptive media bed;
    the impermeable housing having a first end and a second end, wherein the first puncture location and the second puncture location are both located at the first end of the impermeable housing;
    a divider configured to direct the gas from the first puncture location to the second end of the impermeable housing prior to contact of the gas with the adsorptive media bed, and to direct the gas through the adsorptive media bed as it travels from the second end of the impermeable housing to the second puncture location;
    the divider defining a passageway that conducts the gas from the first puncture location to the second end of the impermeable housing prior to contact of the gas with the adsorptive media bed;
    the divider including a tube that extends from the first end of the impermeable housing toward the second end of the impermeable housing, the passageway being defined by an interior of the tube; and
    a diffuser in communication with the passageway and the adsorptive media bed for supplying the gas to the adsorptive media bed.

3. The sieve module of claim 2, further comprising:
    the diffuser including a gas-permeable separator that is connected to the tube and extends transverse to the tube, wherein the adsorptive media bed is disposed between the first end of the impermeable housing and the gas-permeable separator.

4. The sieve module of claim 3, further comprising:
    a gas permeable filler material disposed between the second end of the impermeable housing and the gas-permeable separator.

5. A sieve module, comprising:
    an impermeable housing that is puncturable at a first puncture location to receive gas from an exterior of the impermeable housing and is puncturable at a second puncture location to expel gas to the exterior of the impermeable housing;
    an adsorptive media bed that is disposed within the impermeable housing, wherein the gas flows through the impermeable housing from the first puncture location to the second puncture location by flowing through the adsorptive media bed;

the impermeable housing having a first end and a second end, wherein the first puncture location and the second puncture location are both located at the first end of the impermeable housing; and a crushable material disposed adjacent to the first end of the impermeable housing directly adjacent to the second puncture location.

6. The sieve module of claim 5, wherein the crushable material is interposed between the first end of the impermeable housing and the adsorptive media bed to space the adsorptive media bed from the first end of the impermeable housing.

7. A sieve module, comprising:

an impermeable housing that is puncturable at a first puncture location to receive gas from an exterior of the impermeable housing and is puncturable at a second puncture location to expel gas to the exterior of the impermeable housing;

an adsorptive media bed that is disposed within the impermeable housing, wherein the gas flows through the impermeable housing from the first puncture location to the second puncture location by flowing through the adsorptive media bed;

the impermeable housing having a first end and a second end, wherein the first puncture location and the second puncture location are both located at the first end of the impermeable housing;

the impermeable housing having a first end wall that is located at the first end of the impermeable housing, a second end wall that is disposed at the second end of the impermeable housing, and a peripheral wall that extends from the first end wall to the second end wall; and the impermeable housing including a first portion that defines the first end wall of the impermeable housing and a second portion that defines both the second end wall and the peripheral wall of the impermeable housing, the first portion being a unitary structure, and the second portion being a unitary structure, wherein the first portion of the impermeable housing is connected to the second portion of the impermeable housing to define an interior for the impermeable housing that is sealed with respect to ambient air prior to puncturing of the impermeable housing at the first puncture location or the second puncture location.

8. The sieve module of claim 7, wherein the impermeable housing is fabricated from aluminum.

9. The sieve module of claim 8, further comprising:
the adsorptive media bed including a zeolite material.

10. A portable oxygen concentrator, comprising:

a housing that defines a cavity;

a first puncturing member disposed within the cavity, the first puncturing member capable of supplying a gas;

a second puncturing member disposed within the cavity, the second puncturing member capable of receiving a gas; and a replaceable sieve module having an impermeable housing that is puncturable at a first puncture location to receive gas from an exterior of the impermeable housing and is puncturable at a second puncture location to expel gas to the exterior of the impermeable housing, and an adsorptive media bed that is disposed within the impermeable housing, wherein the gas flows through the impermeable housing from the first puncture location to the second puncture location by flowing through said adsorptive media bed, wherein the replaceable sieve module is received within the cavity of the housing such that the first puncturing member punctures the impermeable housing of the replaceable sieve module at the first location and the second puncturing member punctures the impermeable housing of the replaceable sieve module at the second puncture location.

* * * * *